United States Patent
Wassmer et al.

(10) Patent No.: US 9,765,095 B2
(45) Date of Patent: Sep. 19, 2017

(54) EASILY SYNTHESIZABLE, SPONTANEOUSLY WATER-SOLUBLE, ESSENTIALLY VOC-FREE, ENVIRONMENTALLY FRIENDLY (METH)ACRYLAMIDO-FUNCTIONAL SILOXANOL SYSTEMS, PROCESS FOR PREPARATION THEREOF AND USE

(71) Applicants: Christian Wassmer, Hausen (DE); Burkhard Standke, Loerrach (DE); Thomas Schlosser, Inzlingen (DE); Regina Krause, Rheinfelden (DE)

(72) Inventors: Christian Wassmer, Hausen (DE); Burkhard Standke, Loerrach (DE); Thomas Schlosser, Inzlingen (DE); Regina Krause, Rheinfelden (DE)

(73) Assignee: EVONIK DEGUSSA GmbH, Essen (DE)

( * ) Notice: Subject to any disclaimer, the term of this patent is extended or adjusted under 35 U.S.C. 154(b) by 0 days.

(21) Appl. No.: 15/070,417

(22) Filed: Mar. 15, 2016

(65) Prior Publication Data

US 2016/0222038 A1    Aug. 4, 2016

Related U.S. Application Data

(62) Division of application No. 14/395,750, filed as application No. PCT/EP2013/053651 on Feb. 25, 2013.

(30) Foreign Application Priority Data

Apr. 20, 2012 (DE) .................. 10 2012 206 510

(51) Int. Cl.
C07F 7/18    (2006.01)
C07F 7/08    (2006.01)

(52) U.S. Cl.
CPC .......... *C07F 7/0818* (2013.01); *C07F 7/0834* (2013.01); *C07F 7/184* (2013.01); *C07F 7/1812* (2013.01); *C07F 7/1836* (2013.01); *C07F 7/1892* (2013.01)

(58) Field of Classification Search
CPC .... C07F 7/0818; C07F 7/0834; C07F 7/1892; C07F 7/1836; C07F 7/184
See application file for complete search history.

(56) References Cited

U.S. PATENT DOCUMENTS

| | | | |
|---|---|---|---|
| 3,249,461 A | * | 5/1966 | Te Grotenhuis ........ C03C 25/40 523/203 |
| 3,900,679 A | | 8/1975 | Marzocchi |
| 4,762,759 A | | 8/1988 | Vermeulen et al. |
| 4,927,951 A | | 5/1990 | Kabeta et al. |
| 5,008,349 A | | 4/1991 | Kosal et al. |
| 5,372,841 A | | 12/1994 | Kleyer et al. |
| 5,885,341 A | | 3/1999 | Standke et al. |
| 6,204,403 B1 | | 3/2001 | Pepe et al. |
| 6,641,870 B2 | | 11/2003 | Bartkowiak et al. |
| 6,767,982 B2 | | 7/2004 | Standke et al. |
| 7,834,073 B2 | | 11/2010 | Standke et al. |
| 8,039,110 B2 | | 10/2011 | Jenkner et al. |
| 8,101,682 B2 | | 1/2012 | Standke |
| 8,188,266 B2 | | 5/2012 | Edelmann et al. |
| 8,298,679 B2 | | 10/2012 | Albert et al. |
| 8,394,972 B2 | | 3/2013 | Wassmer et al. |
| 8,481,165 B2 | | 7/2013 | Edelmann et al. |
| 8,728,225 B2 | | 5/2014 | Standke et al. |
| 8,747,541 B2 | | 6/2014 | Scharfe et al. |
| 8,864,895 B2 | | 10/2014 | Albert et al. |
| 8,979,996 B2 | | 3/2015 | Standke et al. |
| 2006/0247329 A1 | | 11/2006 | Moszner et al. |
| 2008/0206572 A1 | | 8/2008 | Edelmann et al. |
| 2009/0005518 A1 | | 1/2009 | Just et al. |
| 2009/0007818 A1 | | 1/2009 | Militz et al. |
| 2012/0321803 A1 | | 12/2012 | Borup et al. |
| 2013/0167754 A1 | | 7/2013 | Wassmer et al. |

FOREIGN PATENT DOCUMENTS

| CN | 101798464 | | 8/2010 |
|---|---|---|---|
| CN | 102405224 | A | 4/2012 |
| EP | 0 222 045 | | 5/1987 |
| EP | 0 425 121 | | 5/1991 |
| EP | 0 621 607 | | 10/1994 |
| EP | 2 277 496 | | 1/2011 |
| JP | 02-149587 | | 6/1990 |
| JP | 07-157490 | | 6/1995 |
| JP | 2003-501435 | | 1/2003 |
| WO | 2010/121873 | | 10/2010 |
| WO | 2011/116206 | | 9/2011 |
| WO | WO 2013/15618 | | 10/2013 |

OTHER PUBLICATIONS

International Search Report Issued Jun. 10, 2013 in PCT/EP13/053651 Filed Feb. 25, 2013.

Thavornyutikarn, B., et al. "Synthesis and Characterization of UV-Curable Poly(dimethylsiloxane) Dimethacrylate", Macromolecular Symposia, vol. 264, No. 1, pp. 144-148, XP0055064752, 2008.

* cited by examiner

*Primary Examiner* — Sudhakar Katakam
(74) *Attorney, Agent, or Firm* — Oblon, McClelland, Maier & Neustadt, L.L.P.

(57) ABSTRACT

The invention relates to a composition and to a process for producing the composition comprising essentially water-soluble (meth)acrylamido-functional siloxanols, and to the use thereof.

5 Claims, No Drawings

US 9,765,095 B2

EASILY SYNTHESIZABLE, SPONTANEOUSLY WATER-SOLUBLE, ESSENTIALLY VOC-FREE, ENVIRONMENTALLY FRIENDLY (METH)ACRYLAMIDO-FUNCTIONAL SILOXANOL SYSTEMS, PROCESS FOR PREPARATION THEREOF AND USE

This application is a Divisional of U.S. application Ser. No. 14/395,750, which was filed on Oct. 20, 2014. U.S. application Ser. No. 14/395,750 is a National Stage of PCT/EP2013/053651, which was filed on Feb. 25, 2013. This application is based upon and claims the benefit of priority to German Application No. 10 2012 206 510.5, which was filed on Apr. 20, 2012.

The invention relates to a composition and to a process for producing the composition comprising (meth)acrylamido-functional siloxanols, preferably essentially water-soluble (meth)acrylamido-functional siloxanols, and to the use thereof.

For the use of glass fibres in fibre composite materials, the glass fibre is frequently surface-treated with functionalized silanes. This is commonly accomplished with the aid of aqueous slips in which the organofunctional silane is dissolved. Depending on the chemical function of the silanes, there may be a positive influence on the desired properties, for example fibre thickness or else cuttability (specifically for short fibre reinforcement). In this case, the organofunctional silanes also make a significant contribution to promoting adhesion between the inorganic fibre and the organic resin. Even though application by means of aqueous slips is desirable, the organofunctional silanes are still prepared in organic solvents.

For example, specific methacryloyl-functionalized silanes, for example 3-methacryloyloxypropyltrimethoxysilane, are used in fibre composite materials, examples being thermosets and thermoplastics, in order to increase the performance of the fibre composite material. In other applications too, such as in filler modification, in coatings or in adhesives/sealants, these functionalized silanes are used as adhesion promoter between organic and inorganic matrix.

A further application lies in the modification of specific properties, for example increasing the cuttability of glass fibres. Some compounds used for that purpose are methacrylamidoalkylalkoxysilanes such as $(RO)_xRSiNH(CO)C(CH_3)=CH_2$ or else chromium(III) methacrylate chlorine complexes, for example Volan® from Du Pont (R=C1-C6 alkyl group).

In order to supply the compounds in aqueous slips, they must have good water solubility. The chromium-based methacrylate compounds exhibit good water solubility. However, they have the disadvantage of containing heavy metals. Methacrylamidoalkylalkoxysilane leads, in an aqueous medium, to hydrolysis of the alkoxy groups and to release of the corresponding alcohols methanol (toxic) and ethanol, and hence to the formation of VOCs (volatile organic compounds).

WO 00/75148 A1 (comparative example 1 here) describes a synthesis proceeding from aminopropyltriethoxysilane with a methacrylate in the presence of dibutyltin oxide (DBTO). This reaction has a number of disadvantages: firstly, for a substantially complete conversion, a 100% excess of methacrylate is used, which has to be distilled off again. Thus, the space-time yield is poor. In addition, the reaction is conducted at high temperatures of 165-170° C., which results in problems because of the tendency of acrylic acid to polymerize. To avoid polymerization, a stabilizer has to be used. Catalysts used for essentially complete conversion are toxic, environmentally damaging organotin compounds, for example dibutyltin oxide (DBTO). A further disadvantage of this process is the costly and inconvenient rectification of the reaction product at high bottom temperatures and very low absolute pressure. For this purpose, a further gas phase stabilizer has to be used in order to avoid polymerization in the column. A heavy metal-containing residue remains in the bottoms, and has to be disposed of separately. The distillation product, the commercially available product Y-5997 from Momentive $(CH_3O)_x(C_2H_5O)_{3-x}Si(CH_2)_3NH(CO)C(CH_3)=CH_2$, is virtually water-insoluble.

U.S. Pat. No. 3,249,461 describes the synthesis of methacrylamidopropylmethoxysilane by the reaction of methacryloyl chloride in inert anhydrous solvents with aminopropyltrimethoxysilane. A disadvantage in this process is the release of an equimolar amount of hydrogen chloride, which has to be removed from the process in a costly and inconvenient manner. In addition, the solvent content reduces the space-time yield. The use of dinitrobenzene as a stabilizer is also disadvantageous.

The problem addressed by the present invention was that of providing (meth)acrylamido-functional organosilicon compounds, which are to have excellent water solubility, and should especially be spontaneously soluble in water. In addition, they should be particularly so environmentally friendly, especially preparable without heavy metal catalysts and/or potentially harmful organic solvents. Equally, the use of stabilizers, as is necessary in the prior art, was to be reduced; more particularly, a process which manages without the use of gas phase stabilizers was to be developed. A further problem was to discover a process which allows preparation in the form of a one-pot reaction. Moreover, one problem was to widen the application spectrum of the (meth)acrylamido-functional organosilicon compounds to be provided, and to open them up to further advantageous applications. A further problem was to better avoid the emission of organic solvents, especially to reduce that of the pure hydrocarbons, and preferably also to greatly reduce VOC release in use as a result of hydrolysis of the alkoxy functions. Moreover, user application was to be distinctly simplified, in that the composition is applicable immediately, optionally after a dilution, and is preferably itself storage-stable in aqueous solution, optionally after a dilution. A further problem addressed was therefore, in contrast to the prior art systems, to avoid the user having to observe long initial preparation times using several components, i.e. addition of water and acid or the like, prior to the use of the (meth)acrylamido-functional organosilicon compounds, and instead being able to use them immediately, optionally after spontaneous dilution in water.

The problem was solved by a controlled aqueous conversion of aminosilanes, especially of aminoalkylalkoxysilanes, preferably of di- and/or triaminoalkyl-functional silanes, in the presence of moisture or aqueous media (synonymous with: in the presence of water), more preferably through hydrolysis and preferably condensation of N-(2-aminoethyl)-3-aminopropyltrialkoxysilane and/or 3-aminopropyltrialkoxysilane to oligomers, also referred to hereinafter as siloxanols for short, and reaction with an acrylic anhydride, especially (meth)acrylic anhydride, in an aqueous medium. The water-soluble acrylamido-functional siloxanols obtained are preferably hydrolysed at least partly, more preferably fully, and optionally essentially freed of alcohol (of hydrolysis). It is a great advantage of the invention that the acrylamido-functional siloxanols thus obtained can preferably be used in the form of a bottom product without further purification. Thus, it is possible with the process according to the invention and the inventive compositions containing acrylamido-functional siloxanes, to supply particularly economically viable and environmentally compatible products.

The invention provides a composition comprising acrylamido-functional siloxanols, especially essentially water-soluble acrylamido-functional siloxanols, derived from a
a) reaction of a component A which is an aminoalkyl-functionalized silicon compound selected from
  (i) an aminoalkyl-functional alkoxysilane or a mixture of aminoalkyl-functional alkoxysilanes, each in the presence of a defined amount of water, or
  (ii) a hydrolysis or condensation product of at least one aminoalkyl-functional alkoxysilane or
  (iii) a mixture comprising at least one aminoalkyl-functional alkoxysilane and a hydrolysis and/or condensation product of at least one aminoalkyl-functional alkoxysilane,
with a component B which is an acrylic anhydride, and optionally
b) removal of at least a portion of the alcohol of hydrolysis, and optionally of at least a portion of the water which was used in (i) and optionally in (ii) or (iii), with optional addition of further water in this step for removal of the alcohol of hydrolysis; preferably, (ii) and (iii) were also prepared by reaction with a defined amount of water.

It was found that, in the case of direct reaction of aminosilanes with acrylic anhydride, the unwanted transesterification products occur, since the methacrylic acid released reacts in a transesterification reaction with the alkoxy groups in the aminosilane.

The inventors have surprisingly succeeded in avoiding these unwanted transesterification reactions which occur in a reaction of aminosilanes with (meth)acrylic anhydride. The unwanted transesterification can be avoided when, before the reaction with (meth)acrylic anhydride, the aminosilanes are oligomerized by hydrolysis and optionally condensation to siloxanes, preferably to siloxanols, with surprisingly successful subsequent acrylamide formation between the aminoalkyl-functional silicon compounds and the (meth)acrylic anhydride.

Preferably, for hydrolysis of the aminoalkyl-functional silanes, a defined amount of water is used, preferably between greater than or equal to 0.1 mol and 4.5 mol, especially between 0.1 and 2.0 mol, of water/mol of silicon atoms (inclusive), preferably between greater than or equal to 0.3 mol and 1.5 mol of water/mol of silicon atoms in the aminoalkyl-functional silicon compounds, particular preference being given to an amount of water between greater than or equal to 0.5 and 1.0 mol of water/mol of silicon atoms.

The bottom temperature in the course of reaction with (meth)acrylic anhydride can be controlled via the rate of dropwise addition of (meth)acrylic anhydride. By cooling the reaction flask, it is possible to achieve quicker addition of (meth)acrylic acid. The maximum possible bottom temperature depends on the stabilizer system in the reaction mixture and the boiling point of the components used.

Essentially water-soluble substances are considered to be acrylamido-functional siloxanols which are water-soluble as such, and can especially be dissolved or correspondingly mixed with water to an extent of at least 3 to 99.9% by weight. Preferred active ingredient concentrations in water are between greater than or equal to 3 to 50% by weight in the overall composition, preferably between greater than or equal to 3 to 40% by weight; particularly preferred alternative concentration ranges are between greater than or equal to 3 to 10% by weight or else between 15 and 45% by weight. The acrylamido-functional siloxanols can be dissolved spontaneously in water and preferably form clear solutions. These solutions are storage-stable, for example over at least three months in a closed vessel at 50° C. In accordance with an alternative, however, acrylamido-functional siloxanols which can be brought into solution by addition of acids, bases or buffers in the aqueous phase and preferably form clear solutions are also considered to be water-soluble.

Particularly preferred compositions comprise acrylamido-functional siloxanols, especially essentially water-soluble acrylamido-functional siloxanols, which are derived from a reaction a) of a component A, an aminoalkyl-functionalized silicon compound selected from (ii) a hydrolysis and/or condensation product of at least one aminoalkyl-functional alkoxysilane or (iii) a mixture comprising at least one aminoalkyl-functional alkoxysilane and a hydrolysis and/or condensation product of at least one aminoalkyl-functional alkoxysilane with a component B which is an acrylic anhydride, especially of the formula IV, and optionally b) removal of at least a portion of the alcohol of hydrolysis, and optionally of at least a portion of the water, with optional addition of further water in this step for removal of the alcohol of hydrolysis. Preferably, the acrylamido-functional siloxanols are admixed with water and the alcohol of hydrolysis is removed until virtually complete hydrolysis of the alkoxy groups has occurred.

According to the invention, it is possible in principle to use any aminoalkoxysilanes for preparation of the hydrolysates and condensates and subsequent reaction with (meth)acrylic anhydride. For the desired improved solubility, preference is given to selecting aminosilanes having one primary and preferably at least one secondary amino group; these at least diamino-functional silanes lead to another improvement in the solubility of the corresponding (meth)acrylamidoalkyl siloxanol. It is an advantage of the additional secondary amino group that it neutralizes the (meth)acrylic acid released in the reaction to form a corresponding salt (aminohydro(meth)acrylate).

The aminohydro(meth)acrylate can be cleaved under basic conditions. Suitable bases are preferably basic alkali metal salts such as NaOH or KOH, preferably alkali metal alkoxides such as NaOR or KOR, preferably where R=alkyl-, preferably methyl-, and particular preference being given to potassium methoxide.

Preferred aminoalkyl-functional alkoxysilanes correspond to the formula I

where the group B in formula I independently corresponds to a group of the formula II

in formula I with $R^1$ independently a linear, branched or cyclic alkyl group having 1 to 8 carbon atoms, especially having 1, 2, 3 or 4 carbon atoms, preferably methyl, ehtyl or propyl, and $R^2$ independently a linear, branched or cyclic alkyl group having 1 to 8 carbon atoms, especially methyl, ethyl, propyl, n-butyl, isobutyl, tert-butyl, pentyl, hexyl, heptyl or octyl, and in formula II with $R^3$ independently a linear, branched or cyclic alkyl, aryl or alkylaryl group having 1 to 8 carbon atoms in formula II, especially methyl, ethyl, butyl or benzyl, where h=0 is particularly preferred; and in formula I a is independently 0 or 1, b is independently 0, 1 or 2, b preferably being 0, and in formula II c is independently selected from 1, 2, 3, 4, 5 and 6, d is independently selected from 1, 2, 3, 4, 5 and 6, e is independently selected from 0, 1, 2, 3, 4, 5 and 6, f is independently selected from 1, 2, 3, 4, 5 and 6, g is independently selected from 0, 1, 2, 3, 4, 5 and 6, and h is independently 0 or 1; alternatively preferably e=g=0 or 1, and d=f=2 or 3 and h=0 with c=3 and b=0 and a=0; particularly preferred combinations are with $R^1$ being methyl or ethyl, a=0 and b=0 with c=3 and g, e and h each=0; alternatively likewise preferably, a=0, b=0, c=3, e=1, d=1, 2 or 3, preferably d=2, and g=0, h=0, for diamino-functional silanes, or the B group corresponds to the formula III

$$-(CH_2)_f-NH_{2-p}(CH_2-CH_2-NH_2)_p \quad \text{(III)}$$

with j=1, 2 or 3 and p=0, 1 or 2, p preferably being selected from 1 and 2; if appropriate, p may also be 0.

It is generally preferable when the aminoalkyl-functional alkoxysilane corresponds to a diaminoalkyl-functional or a triaminoalkyl-functional silane, preferably a diaminoalkyl-functional or a triaminoalkyl-functional alkoxysilane of the formula I. Likewise particularly preferred are mixtures of the aforementioned silanes, such as aminosilane with diaminosilane or else aminosilane with triaminosilane or diaminosilane with triaminosilane, or else mixtures comprising three or more different aminosilanes of the formula I.

The acrylic anhydrides used are preferably methacrylic acid or (unsubstituted) acrylic anhydride, more preferably of the formula IV $$(CHR^5=CR^4CO)_2O \quad \text{(IV)}$$

where $R^4$ is independently a hydrogen atom or a methyl group and $R^5$ is independently a hydrogen atom or a methyl group, $R^5$ preferably being a hydrogen atom. Preference is given to $(CH_2=C(CH_3)CO)_2O$ and $(CH_2=CHCO)_2O$.

The inventive composition, which can be obtained from the conversion of (i), (ii) and/or (iii), can be represented in idealized form by the general idealized formula V below for at least one essentially water-soluble acrylamido-functional siloxanol, where the acrylamido-functional siloxanols may preferably have linear, cyclic and crosslinked structures,

$$(R^1O)[(R^1O)_{1-a}(R^2)_aSi(C)_{1+b}O]_u[(Y)Si(C)_{1+b}O]_{u'}R^1 \cdot (HX)_z \quad \text{(V)},$$

where, in the general formula V,

C is an acrylamido group and

Y corresponds to $OR^1$ or, in crosslinked and/or three-dimensionally crosslinked structures, independently to $OR^1$ or $O_{1/2}$, where $R^1$ corresponds essentially to hydrogen or some of $R^1$ may optionally also independently be a linear, branched or cyclic alkyl group having 1 to 8 carbon atoms, $R^1$ being an alkyl preferably to an extent of less than 10 mol %, preferably less than 5 mol %, more preferably less than 2 mol %, preferably less than or equal to 1 mol %, and $R^2$ corresponds to a linear, branched or cyclic alkyl group having 1 to 8 carbon atoms, especially according to the definition of formula (I), HX is an acid, where X is an inorganic or organic acid radical, with each a independently 0 or 1, each b independently 0 or 1 or independently additionally optionally 2, b preferably being 0, with each u independently an integer greater than or equal to 2, u' greater than or equal to 0 and z greater than or equal to 0 and (u+u')≥2, z especially being 0 or greater than or equal to 1, where z may preferably be less than to equal to the number of secondary nitrogen atoms in the aminosilane used, and z may likewise preferably be greater than the number of secondary nitrogen atoms, where the composition is essentially free of diluent, especially organic solvents, more preferably of protic organic solvents, and releases essentially no more alcohol in the course of crosslinking.

Preferably, u on average is selected from an integer from 2 to 500, especially from 2 to 150, preferably from 2 to 80, including all numerical values inbetween, such as 2, 3, 4, 5, 6, 7, 8, 9, 10, 15, 20, 25, 30, 35, 40, 45, 50, 55, 60, 65, 70, 75 and 80, and in each case with a range of variation of up to plus/minus 5, u preferably being between greater than or equal to 20 and 80, more preferably between 20 and 60, preferably between greater than or equal to 20 and 40. In this context, independently thereof, u' on average may be selected from an integer between 0 and 200, especially from 0 to 100, preferably from 0, 1, 2, 3, 4, 5, 6, 7, 8, 9, 10, 15, 20, 30, 35, 40, 45, 50, 55, 60, 65, 70, 75, 80 and 85, and in each case with a range of variation of up to plus/minus 5, u' preferably being between greater than or equal to 10 and 40, preferably 10 to 35. More preferably, the sum of (u+u') together on average is between greater than or equal to 5 and 100, especially between greater than or equal to 20 and 75, such as around 25 to 60.

A useful HX is acrylic acid or else any other organic or inorganic acid suitable for the later use. It is generally possible to remove the acrylic acid present in the composition if required. It can preferably remain in the composition, bound via hydrogen bonds or as a salt, and contribute to crosslinking of the product, for example as a comonomer, in a later use.

Illustrative acrylamido groups (group C) on the silicon atoms of the siloxanols are described as examples hereinafter, each on a silicon atom:

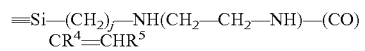

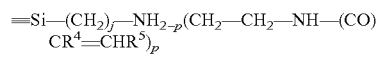

In principle, an acrylamido group (group C), especially an acrylamido group of the siloxanols, is understood to mean all conceivable conversions of the aminoalkyl-functional groups mentioned with (meth)acrylic anhydride or $CHR^5=CR^4(CO)-$, but especially those formed from a reaction of an amino-functional group B according to the formula II and/or III with an acrylic anhydride of the formula IV. Thus, a C group may be selected from

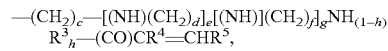

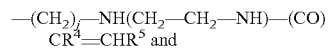

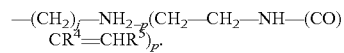

The invention likewise provides a process for preparing a composition comprising acrylamido-functional siloxanols, especially essentially water-soluble acrylamido-functional siloxanols, and compositions obtainable by this process, by conducting the process in at least one step in the presence of water, preferably of a defined amount of water, and reacting a component A, an aminoalkyl-functional silicon compound selected from:
- (i) at least one aminoalkyl-functional alkoxysilane or a mixture of aminoalkyl-functional alkoxysilanes of the formula I, defined as above, or
- (ii) a hydrolysis or condensation product of at least one aminoalkyl-functional alkoxysilane of the formula I or
- (iii) a mixture comprising at least one aminoalkyl-functional alkoxysilane of the formula I and a hydrolysis and/or condensation product of at least one aminoalkyl-functional alkoxysilane of the formula I, with a component B, an acrylic anhydride of the formula IV, defined as above, especially methacrylic anhydride or the (unsubstituted) acrylic anhydride, and optionally at least partly removing the alcohol of hydrolysis formed in the reaction.

Preferably, the reaction is conducted in the presence of a diluent, preference being given to an organic protic diluent such as alcohol.

It is preferable in this case when the defined amount of water is established in a process step prior to the step of reaction with component B, especially for preparation of components A (ii) or (iii) from (i).

According to the invention, it is unnecessary to further purify the compositions obtained; more particularly, a complex distillative workup of the acrylamido-functional siloxanols is unnecessary, since the bottom products can preferably be used directly. The inventive bottom products do not require any further purification because no disruptive catalysts or disruptive stabilizers are present in the bottom products. Consequently, the inventive compositions can be prepared in a much more economically viable manner and with more environmentally compatible starting substances than described in the prior art.

It is a particular advantage of the process according to the invention that there is no need to use any gas phase stabilizers, as necessary in the prior art, because the inventive process regime allows direct use of the composition in the form of the bottom product. A complex rectification of the products as in the prior art can be dispensed with. Consequently, the inventive compositions can be prepared in a much more economically viable manner and with more environmentally compatible starting substances than described in the prior art.

It is a further advantage of the inventive compositions that they enable shorter preparation times on the part of the user prior to use. Thus, the user can bring the inventive composition to the desired concentration in a simple manner with water; it dissolves spontaneously and forms a clear solution. Simple stirring accelerates dissolution in water. It is possible to dispense with the addition of further chemicals, as in the prior art, acid, etc.

In preferred embodiments, the process is preferably conducted with an aminoalkyl-functional silicon compound selected from an aminoalkyl-functional alkoxysilane of the formula I, or a hydrolysis or condensation product of at least one aminoalkyl-functional alkoxysilane of the formula I, or a mixture comprising at least one aminoalkyl-functional alkoxysilane of the formula I and a hydrolysis and/or condensation product of at least one aminoalkyl-functional alkoxysilane of the formula I, the hydrolysis and/or condensation of the aminoalkyl-functional alkoxysilane of the formula I being effected in the presence of a defined amount of water, the defined amount of water preferably corresponding to 0.1 to 2.0 mol of water per mole of silicon atoms in the aminoalkyl-functional silicon compound used in the process, especially of the formula I, preferably 0.3 to 1.5 mol of water per mole of silicon atoms in the aforementioned silicon compound, more preferably 0.5 to 1.0 mol of water per mole of silicon atoms in the silicon compound; preferably, the defined amount of water is established in a process step prior to the step of the reaction with the component B and is preferably at least partly consumed by the hydrolysis.

In preferred embodiments, the process is preferably conducted with an aminoalkyl-functional alkoxysilane of the formula I, or a hydrolysis or condensation product of at least one aminoalkyl-functional alkoxysilane of the formula I or a mixture comprising at least one aminoalkyl-functional alkoxysilane of the formula I and a hydrolysis and/or condensation product of at least one aminoalkyl-functional alkoxysilane of the formula I a) with $R^1$ independently methyl or ethyl and with a=0 and b=0 with c=1, 2 or 3 and with the group B of the formula II with g=0 and e=1 and h=0, d=1, 2, 3, preferably d=2, or b) with $R^1$ independently methyl or ethyl and with a=0 and b=0 with c=3 and with the group B of the formula II with g, e and h each 0 or, in an alternative, with a=0, b=0, c=3, and with the group B of the formula II with e=1, d=1, 2, 3, preferably d=2 and with g=0, h=0 or with the group B of the formula II with e=g=0 or 1, and d=f=2 or 3 and h=0 with c=3 or with the group B of the formula III with j=3 and p=1 or 2, or c) with $R^1$ independently methyl or ethyl and with a=0 and b=0 with c=2 and with the group B of the formula II with g, e and h each 0 or, in an alternative, with a=0, b=0, c=3, and with the group B of the formula II with e=1, d=1, 2, 3, preferably d=2 and with g=0, h=0 or with the group B of the formula II with e=g=0 or 1, and d=f=2 or 3 and h=0 with c=2 or with the group B of the formula III with j=3 and p=1 or 2, or d) with $R^1$ independently methyl or ethyl and with a=0 and b=0 with c=1 and with the group B of the formula II with g, e and h each 0 or, in an alternative, with a=0, b=0, c=3, and with the group B of the formula II with e=1, d=1, 2, 3, preferably d=2 and with g=0, h=0 or with the group B of the formula II with e=g=0 or 1, and d=f=2 or 3 and h=0 with c=1 or with the group B of the formula III with j=3 and p=1 or 2.

It is likewise preferable when the process is preferably conducted with an aminoalkyl-functional alkoxysilane, or a hydrolysis or condensation product of at least one aminoalkyl-functional alkoxysilane or a mixture comprising at least one aminoalkyl-functional alkoxysilane and a hydrolysis and/or condensation product from at least one aminoalkyl-functional alkoxysilane selected from the following aminoalkyl-functional alkoxysilanes, especially of the general formula I: 3-aminopropyltrimethoxysilane, 3-aminopropyltriethoxysilane: 3-aminopropylmethyldimethoxysilane, 3-aminopropylmethyldiethoxysilane, 1-aminomethyltrimethoxysilane, 1-aminomethyltriethoxysilane, 2-aminoethyltrimethoxysilane, 2-aminoethyltriethoxysilane, 3-aminoisobutyltrimethoxysilane, 3-aminoisobutyltriethoxysilane, N-n-butyl-3-aminopropyltriethoxysilane, N-n-butyl-3-aminopropylmethyldiethoxysilane, N-n-butyl-3-aminopropyltrimethoxysilane, N-n-butyl-3-aminopropylmethyldimethoxysilane, N-n-butyl-1-aminomethyltriethoxysilane, N-n-butyl-1-aminomethylmethyldimethoxysilane, N-n-butyl-1-aminomethyltrimethoxysilane, N-n-butyl-1-aminomethylmethyltriethoxysilane, benzyl-3- aminopropyltrimethoxysilane, benzyl-3-aminopropyltriethoxysilane, benzyl-2-aminoethyl-3-aminopropyltrimethoxysilane, benzyl-2-aminoethyl-3-aminopropyltriethoxysilane, diaminoethylene-3-propyltrimethoxysilane, diaminoethylene-3-propyltriethoxysilane, triaminodiethylene-3-propyltrimethoxysilane, triaminodiethylene-3-propyltriethoxysilane, (2-aminoethylamino)ethyltrimethoxysilane, (2-aminoethylamino)ethyltriethoxysilane, (1-aminoethylamino)methyltrimethoxysilane and (1-aminoethylamino)methyltriethoxysilane, preference being given especially to di- and/or triaminoalkoxysilanes. Particular preference is given to diaminoethylene-3-propyltrimethoxysilane, diaminoethylene-3-propyltriethoxysilane, triaminodiethylene-3-propyltrimethoxysilane, triaminodiethylene-3-propyltriethoxysilane.

It is additionally particularly preferable when the process is conducted in at least one step in the presence of a defined amount of water; more particularly as follows:

component A, an aminoalkyl-functional silicon compound selected from: (i) at least one aminoalkyl-functional alkoxysilane or a mixture of aminoalkyl-functional alkoxysilanes of the formula I, defined as above, is reacted with a defined amount of water or water in excess or (ii) a hydrolysis or condensation product of at least one aminoalkyl-functional alkoxysilane of the formula I is prepared from the aminoalkyl-functional alkoxysilane of the formula I in the presence of a defined amount of water, (iii) a mixture comprising at least one aminoalkyl-functional alkoxysilane of the formula I and a hydrolysis and/or condensation product of at least one aminoalkyl-functional alkoxysilane of the formula I, is prepared from the aminoalkyl-functional alkoxysilane in the presence of a defined amount of water, and b) subsequently reacted with a component B, an acrylic anhydride of the formula IV, defined as above, especially methacrylic anhydride or the (unsubstituted) acrylic anhydride, and c) optionally, the alcohol of hydrolysis formed in the reaction is at least partly removed.

In further preferred process variants, preference is given to processes comprising in a step (I) comprising the component steps which follow, admixing component A, an aminoalkyl-functional silicon compound, which is preferably at least one aminoalkyl-functional alkoxysilane of the formula I as defined above, optionally in a mixture with a diluent, especially organic protic diluents, preferably an alcohol, more preferably methanol, ethanol or propanol, with a defined amount of water, preference being given to continuous or discontinuous metered addition of water; preferably 0.5 to 1.5 mol and more preferably 0.5 to 1.0 mol of water per mole of silicon atoms in the silicon compound are metered in; preferably within a defined period, and preferably with stirring, preference within the temperature range of 0 to 75° C., especially 30 to 75° C., preferably between 40 and 65° C., more preferably between 50 and 65° C., for between 10 minutes and 10 hours, preferably between 10 minutes and 5 hours, more preferably between 10 minutes and 2.5 hours, and optionally at least partly removing the alcohol of hydrolysis and/or the added diluent, preferably the alcohol added, and adding the acrylic anhydride of the formula IV to the resulting mixture, especially at a temperature of the mixture between 0 and 30° C., preferably metering in the acrylic anhydride of the formula IV such that the temperature of the mixture does not rise above 75° C., and optionally adding a stabilizer to the mixture, and, in step II, alternatively, conducting step (IIa) or step (IIb), wherein in a step (IIa), in an alternative, after step (I), at least partly removing the alcohol of hydrolysis and/or the added diluent under ambient or reduced pressure and elevated temperature, preference being given to adding water in step (IIa), and water can especially be added before, during and after further addition of diluent, or in a step (IIb), in a further alternative, after step (I), adding a base to the mixture, especially when the acrylic anhydride is present in a molar excess relative to the primary amino groups of the aminoalkyl-functional silane, preferably a base which forms a salt with acrylic acid which is sparingly soluble in water or in the alcoholic-aqueous phase, for example a metal salt, alkaline earth metal hydroxide, alkaline earth metal oxide or alkali metal hydroxide, and optionally removing the precipitate, especially the sparingly soluble salt of the acrylate, optionally adding an organic acid and at least partly removing the alcohol of hydrolysis and/or the diluent and optionally removing at least a portion of the water, with optional addition of further water for removal of the alcohol of hydrolysis in this step. The composition thus obtained can be used directly; preferably, it is adjusted with water to the desired active ingredient content of acrylamido-functional siloxanol. Formation of sparingly soluble salts can also be accomplished by using alkali metal or alkaline earth metal hydroxides or oxides such as calcium hydroxide, calcium oxide, but it is also possible to use sodium hydroxide/oxide. In general, the salts of Ca, Mg, Ba, Sr, Al and/or zinc can be used to form sparingly soluble salts.

Useful diluents generally include all suitable diluents, such as organic aprotic or protic diluents and mixtures of these, examples being alcohols, ethers or ketones, ethyl acetate, methylene chloride, preference being given to organic protic diluents or, for dilution of the composition prepared, water. The alcohol (of hydrolysis) already present as a diluent and/or formed in the reaction is removed substantially, preferably completely, in all process variants according to the invention. The distillative removal of the alcohol is carried out preferably under reduced pressure. Alternatively, until an alcohol content of less than 20% by weight to 0.0001% by weight, preferably less than or equal to 12% by weight, more preferably less than or equal to 5% by weight, especially preferably less than or equal to 3.0% by weight, even more preferably less than or equal to 1.0% by weight, especially less than or equal to 0.5% by weight is detected, or down to the current analytical detection limit. Generally speaking, the resulting composition of the invention is then substantially solvent-free, more particularly alcohol-free. The composition obtained accordingly preferably corresponds directly to the composition of the invention, and preferably need not itself be further purified.

It is especially preferable when the volatile diluent and the alcohol of hydrolysis are removed down to a content in the overall composition of less than or equal to 12% by weight to 0% by weight, preferably to less than or equal to 10% by weight, more preferably less than or equal to 5% by weight, even more preferably less than or equal to 2% by weight to 0.0001% by weight, especially less than or equal to 1 to 0.0001% by weight, the removal preferably being effected by distillation, especially under reduced pressure in the range from 1 to 1000 mbar, preferably from 0.001 to 350 mbar, more preferably between 0.001 and 250 mbar, at a mild temperature of bottom temperature less than 60° C., especially less than 55° C.

Preferably, in the process, the molar ratio of the nitrogen atoms in the aminoalkyl-functional silicon compound, especially in the aminoalkyl-functional silanes of the formula I, to the molar ratio of the $CHR^5=CR^4(CO)$— acryloylcarbonyl function released from the acrylic anhydride of the formula IV is in the range from 1:5 to 5:1, especially 1:2 to 2:1, preferably 1:1.5 to 1.5:1, more preferably 1:1 with a range of variation of plus/minus 0.5, preferably plus/minus 0.2.

Alternatively, it may be particularly preferable to use a diaminoalkyl-functional silane in an equimolar amount with acrylic anhydride of the formula IV. The function of the secondary amine function here is to neutralize the free acrylic acid, and can react to give an aminohydro(meth)acrylate, which can especially be cleaved subsequently under basic conditions.

Preference is further given to a process wherein the active ingredient content of acrylamido-functional siloxanols is adjusted to 0.0001 to 99.9% by weight in the overall composition, especially to 10 to 80% by weight, preferably to 20 to 60% by weight, more preferably to 35 to 60% by weight, where the active ingredient content can be adjusted to any value between 99.99% by weight and 0.00001% by weight by dilution with a diluent, preferably with water or optionally with aqueous alcohols or any other suitable diluent.

It is likewise possible to add customary acids, bases, additives, auxiliaries, fillers, stabilizers, pigments, to adjust the product properties or the colour, or to increase storage stability.

The process according to the invention affords compositions generally having pH values, after the removal of the diluent, alcohol of hydrolysis and at least portions of water, having a value between 3 and 11, preferably between 5 and 11, especially between 6 and 10, more preferably between 6 and 8, especially preferably between 7 and 8, or between 6.5 and 8.0 or between 8 and 10. It is particularly preferable in this context when the compositions produced comprise (meth)acrylamidoalkyl-functional siloxanols which have good water solubility without modification of the pH. These compositions then typically have a pH of 6 to 9.

Additionally or alternatively, the pH of the composition can be adjusted by adding an acid or base. Preferably, the pH of a composition can be adjusted to a pH below 8 in the aqueous phase, more preferably between 3 and 8, especially between 3 and 6, preferably between 3 and 5.5, more preferably between 3 and 5.0. Typical acids for adjusting the pH may be mineral acid such as HCl, sulphuric acid or else organic acids, preference being given to organic acids such as acetic acid, lactic acid or formic acid.

The preparation process likewise has an advantageous effect on the viscosity of the compositions. Thus, the inventive compositions prepared are high-mobility liquids of a viscosity which allows easy processing, simple transfer and measurement. The viscosity of the compositions—prepared as the bottom product—is between 1 mPas and 2000 mPas, preferably between 1 and 1500 mPas, further preferably between 1 and 400 mPas.

The invention likewise provides compositions obtainable by an aforementioned process and comprising acrylamido-functional siloxanols, preferably essentially water-soluble acrylamido-functional siloxanols, especially acrylamido-functional siloxanols which have been at least partly to preferably essentially fully hydrolysed, the composition further comprising amlamidoalkyl-aminoalkyl-functional siloxanols and optionally acrylamidoalkyl-aminoalkyl-functional silanols.

The invention further provides for the use of a composition and of the process products as an adhesion promoter, for functionalization of glass, especially for functionalization of glass fibres, for modification of fillers, pigments and/or inorganic surfaces, especially as a filler coating, coating of pigments, coating of inorganic surfaces, in dental impression compounds, in dental polymer compounds, as an additive in polymers, in adhesives, in sealants, in fibre composite materials, together with polymers, especially thermoplastics, thermosets, elastomers, for functionalization of polymers, for adjusting the hydrophilicity of polymers. Particular preference is given to use for production of aqueous systems comprising the inventive acrylamido-functional siloxanols, or materials, articles and/or products modified thereby.

The example which follows illustrates the process according to the invention in detail without limiting the invention to this example.

Determination Methods:

The alcohol content after hydrolysis is determined by gas chromatography (% by weight). $SiO_2$ content of organic silicon compounds: determined by processes known to those skilled in the art, for example oxidation of the organic constituents, followed by calcination, hydrofluoric acid fuming and determination of the weight difference (%=% by weight).

Determination of nitrogen: By a method known to those skilled in the art, for example according to Kjeldahl. Turbidity: DIN EN ISO 7027, with instrument from HACH Lange, model 2100 ISO.

Compounds Used:

"TEMPO (=2,2,6,6-tetramethylpiperidinyloxy free radical)" and "4-hydroxyTEMPO";

"SANTONOX (Flexsys America, Akron, Ohio) antioxidant 4,4'-thio-bis (6-t-butyl-m-cresol)"

EXAMPLE 1

A 500 ml stirred apparatus with distillation system was initially charged with 156.00 g of N-(3-(trimethoxysilyl)propyl)ethylenediamine (0.70 mol) and 40.20 g of methanol. 9.52 g of demineralized water (0.53 mol) were added dropwise within 6 minutes while stirring. In the course of this, the bottom temperature rose to 47.8° C. The mixture was stirred at a bottom temperature of 54° C. to 59° C. for a further 2 hours. At a bottom temperature of 23.1° C., 107.9 g of methacrylic anhydride (0.70 mol) were added dropwise within 2 hours. In the course of this, the bottom temperature rose to max. 51.7° C. 0.02 g of 4-hydroxy-tempo was added to the bottoms as an additional stabilizer. Subsequently, 30.21 g of distillate were removed at an absolute pressure of about 200 mbar and a bottom temperature of about 40° C. The methanol content of the distillate was 98.3 area % (GC-TCD determination). The viscosity in the bottoms distinctly increased. For further analysis, 78.1 g of sample were taken from the bottoms. Subsequently, at a bottom temperature of 32.2° C., 99.61 g of water were added within two minutes. In the course of this, the bottom temperature rose to 36.3° C. 45.2 g of methanol/water mixture were distilled off at an absolute pressure of 200 mbar and a bottom temperature of about 49° C. Subsequently, 120.02 g of water were stirred in, and 106.02 g of methanol/water mixture were distilled off at an absolute pressure of 200 mbar to 128 mbar. A clear, slightly viscous, yellowish liquid was obtained as the bottom product. Yield: 227.9 g. As can be seen in Table 1, the product has a solids content of 54.6%.

TABLE 1

Analysis results for the bottom product from Example 1

| Determination | Method | Result |
|---|---|---|
| Total N [%] | see above | 5.2 |
| Solids content [%] | 3 g/3 hours/105° C. | 54.6 |
| $SiO_2$ content [%] | see above | 11.6 |
| pH | DIN ISO 4925 | 7.7 |
| Density [g/cm$^3$] | DIN 51757 | 1.142 |
| Viscosity [mPa · s] | DIN 53015 | 351 |
| Free methanol [%] | see above | 0.1 |
| $^1$H and $^{13}$C NMR | The singly converted oligomerized target product was found. Amidation has been effected at the primary amine. | |

EXAMPLE 2

An 8 l stirred apparatus with distillation system was initially charged with 2490.58 g of N-(3-(trimethoxysilyl)propyl)ethylenediamine (11.2 mol) and 640.92 g of methanol. 161.54 g of demineralized water (8.96 mol) were added dropwise within 11 minutes while stirring. In the course of this, the bottom temperature rose to 54.7° C. The mixture was stirred at a bottom temperature of 51° C. to 56° C. for a further 0.8 hour. At a bottom temperature of 36.3° C., a solution of 1727.24 g of methacrylic anhydride (11.2 mol) and 3.40 g of 4-hydroxy-tempo was then metered in within 2.4 hours. In the course of this, the bottom temperature rose to max. 53.6° C. The bottoms remained clear and colourless. Subsequently, 2400.32 g of demineralized water were metered in within 14 minutes. Free methanol was distilled off at an absolute pressure of about 200 mbar to 112 mbar. The bottom temperature during the distillation was 46.0° C. to 52.2° C. The total amount of distillate was 2819.3 g. During the distillation, a total of 3699.72 g of demineralized water were added in four portions. A clear, only slightly yellowish, low-viscosity liquid was obtained as the bottom product. Yield: 8082.3 g. As can be seen in Table 2, the product has a solids content of 40.6%.

TABLE 2

Analysis results for the bottom product from Example 2

| Determination | Method | Result |
|---|---|---|
| Total N [%] | see above | 4.1 |
| Solids content [%] | 3 g/3 hours/105° C. | 40.6 |
| $SiO_2$ content [%] | see above | 8.3 |
| pH | DIN ISO 4925 | 7.1 |
| Density [g/cm$^3$] | DIN 51757 | 1.097 |
| Viscosity [mPa · s] | DIN 53015 | 20 |
| Free methanol [%] | see above | 1.4 |
| $^1$H and $^{13}$C NMR | The singly converted oligomerized target product was found. Amidation has been effected at the primary amine. | |

COMPARATIVE EXAMPLE 1 (comparative example for WO 00/75148 A1)

A 1 l stirred apparatus with distillation system was initially charged with 398.07 g of aminopropyltriethoxysilane (1.8 mol), and 1.99 g of dibutyltin oxide, 0.037 g of ionol and 0.18 g of 4,4'-thiobis(6-tert-butyl-m-cresol) were stirred in. Subsequently, within 2 hours, a mixture of 360.35 g of methyl methacrylate (3.60 mol) and 5.41 g of dipropylamine was metered in at a bottom temperature of 152.8° C. to 165.5° C. After a reaction time of 0.3 hour, at a top temperature of 76.5° C. to 80.4° C., a mixture of methanol, ethanol, methyl methacrylate and ethyl methacrylate was removed. After a distillation time of 2.5 hours, at an absolute pressure of 316 mbar to <1 mbar and a bottom temperature of 157.2° C., residual amounts of low boilers were removed from the bottom product. A total of 287.8 g of distillate was removed. 461.35 g of pale yellowish and low-viscosity liquid were obtained as the bottom product. In accordance with the disclosure of WO 00/75148 A1, the crude methacrylic product is distilled under high vacuum. For the purposes of determining the solubility, it was entirely sufficient to use the crude product that still contains dibutyltin oxide. For later use, a rectification disclosed by WO 00/75148 A1 would be necessary.

TABLE 3

Analysis results from Comparative Example 1

| Determination | Method | Result |
|---|---|---|
| Total N [%] | see above | 5.0 |
| $SiO_2$ content [%] | see above | 22.0 |
| Free methanol [%] | see above | 0.1 |
| pH | DIN ISO 4925 | 9.7 |
| Viscosity [mPa · s] | DIN 53015 | 50.1 |

Solubility Characteristics:

Table 4 shows the solubility characteristics as a function of the aminosilane used in the reaction with methacrylic anhydride. Bottom products from Example 1 and Example 2 show good solubility (dissolve spontaneously within a few seconds and lead to clear mixtures) even in the case of direct dissolution in demineralized water (without addition of acetic acid). The bottom product from Example 2 shows good solubility characteristics even at distinctly increased concentrations. In comparison, the product from Comparative Example 1, and also the commercially available Y-5997 (Momentive Performance Materials, mixture of 2-methacrylamidoalkoxypropylsilane having ethoxy and methoxy groups as alkoxy groups), does not dissolve in demineralized water (Table 6). Only at low pH values does this product show solubility after vigorous stirring for 10 minutes (Table 7).

TABLE 4

Overview of the solubility tests of the bottom products (3.0% bottom product in demineralized water)

| | pH | Turbidity [FNU] | | |
|---|---|---|---|---|
| Bottom product from Example | (hydro-lysate) | after 1 min. | after 1 h | after 24 h |
| 1 (reactant: N-(3-(tri-methoxysilyl)propyl)-ethylenediamine | 7.3 | clear | clear (0.3 FNU) | clear (0.5 FNU) - after storage at RT for 6 d |
| 1 | 4.1[1)] | clear | clear (0.3 FNU) | clear (1.0 FNU) - after storage at RT for 7 d |

TABLE 4-continued

Overview of the solubility tests of the bottom products
(3.0% bottom product in demineralized water)

| Bottom product from Example | pH (hydrolysate) | Turbidity [FNU] | | |
|---|---|---|---|---|
| | | after 1 min. | after 1 h | after 24 h |
| 2 (reactant: N-(3-(tri-methoxysilyl)propyl)ethylene-diamine | 5.4[1)] | clear | clear (1.1 FNU) | clear (0.9 FNU) |

[1)]The pH of the hydrolysate was adjusted by addition of acetic acid.

TABLE 5

Overview of the solubility tests on
the bottom product from Example 2

| Hydrolysate | | | Turbidity [FNU] | |
|---|---|---|---|---|
| w(bottom product) [%] | w(H$_2$O) [%] | pH | 1 min. | 24 h |
| 6 | 94 | 6.8 | 0.7 (clear) | 0.6 (clear) |
| 12 | 88 | 6.7 | 0.9 (clear) | 0.9 (clear) |

* w = weight

TABLE 6

Solubility of 3% of the product from Comparative
Example 1 and Y-5997 in demineralized water

| Product | pH (hydrolysate) | Turbidity [FNU] | | |
|---|---|---|---|---|
| | | after 10 min. | after 1 h | after 24 h |
| Y-5997 | 9.1 | not dissolved | turbid/ precipitates | turbid/ precipitates |
| From Example 3 | not determined | not dissolved | turbid/ precipitates | turbid/ precipitates |

TABLE 7

Solubility of 3% Y-5997 in demineralized water. The pH of
the hydrolysate was adjusted by addition of acetic acid.

| pH (hydrolysate) | Turbidity [FNU] | | | |
|---|---|---|---|---|
| | after 1 min. | after 10 min. | after 1 h | after 24 h |
| 4.1 | turbid | clear | clear (0.3 TE/F) | clear (1.7 FNU) - after storage at RT for 7 d |

VOC Release as a Function of Active Ingredient Concentration:

As is apparent in Table 8, Y-5997 has a maximum VOC release of 18% at a 40% active ingredient concentration. The methacrylamidopropylsiloxanol from Example 2 releases only max. 1.4% VOC at the same active ingredient concentration.

TABLE 8 comparison of maximum VOC release as a function
of active ingredient concentration

| Active ingredient concentration [w/w %] | VOC [w/w %] | |
|---|---|---|
| | Y-5997 | Methacrylamido-propylsiloxane from Example 2 |
| 40 | 18 | 1.4 |
| 20 | 9.0 | 0.7 |
| 3 | 1.35 | 0.11 |

* w = weight

TABLE 9

Calculation of maximum VOC release

| Determination | Method | Unit | Methacrylamido-propylsiloxane from Example 2 | Y-5997 |
|---|---|---|---|---|
| Methanol after hydrolysis | see above | w/w % | 1.4 | 34 |
| Ethanol after hydrolysis | see above | w/w % | <0.1 | 11 |
| VOC | Sum total of methanol/ethanol after hydrolysis | w/w % | 1.4 | 45 |

* w = weight

Solubility and Maximum VOC Release as a Function of Active Ingredient Concentration:

As apparent in Table 10, Y-5997 shows poor solubility at relatively high active ingredient concentrations in water/acetic acid. The addition of acetic acid helps to dissolve the Y-5997 at low active ingredient concentrations in water. For this purpose, however, the hydrolysate has to be stirred vigorously for 8 minutes. The methacrylamidopropylsiloxanol from Example 2 shows spontaneous solubility even at a high active ingredient concentration. Addition of acetic acid is unnecessary (see Table 11).

TABLE 10

Solubility and maximum VOC release from Y-5997 as
a function of active ingredient concentration

| Active ingredient concentration [w/w %] | VOC [w/w %] | Dissolution characteristics |
|---|---|---|
| 40 | 18 | Product is insoluble in demineralized water. However, the hydrolysate still remains distinctly turbid in 1.50% acetic acid. |
| 20 | 9.0 | Product is insoluble in demineralized water. However, the hydrolysate still remains distinctly turbid in 1.50% acetic acid. |
| 3 | 1.35 | A clear hydrolysate is obtained in 1.50% acetic acid after vigorous stirring for 8 min. |

* w = weight

TABLE 11

Solubility and maximum VOC release from methacrylamidopropylsiloxanol (Example 2) as a function of active ingredient concentration:

| Active ingredient concentration [w/w %] | VOC [w/w %] | Dissolution characteristics |
|---|---|---|
| 40 | 1.40 | Product was not diluted |
| 20 | 0.70 | Dissolves spontaneously in water: clear liquid, unchanged after 4 d |
| 8 | 0.28 | Dissolves spontaneously in water: clear liquid, unchanged after 4 d |
| 3 | 0.11 | Dissolves spontaneously in water: clear liquid, unchanged after 4 d |

* w = "weight"

TABLE 13

Overview of the solubility tests for Example 3

| Hydrolysate | | | Turbidity [FNU] | |
|---|---|---|---|---|
| w(bottom product) [%] | w(H2O) [%] | pH | 1 min. | 24 h |
| 6 | 94 | 6.8 | 2.9 (clear) | 1.6 (clear) |
| 12 | 88 | 6.7 | 3.1 (clear) | 2.7 (clear) |

| Hydrolysate | | | Turbidity [FNU] | |
|---|---|---|---|---|
| w(bottom product) [%] | w(0.5% acetic acid) [%] | pH | 1 min. | 24 h |
| 6 | 94 | 5.1 | 1.7 (clear) | 1.7 (clear) |
| 12 | 88 | 4.2 | 1.7 (clear) | 2.6 (clear) |

EXAMPLE 3

A 1 l stirred apparatus with distillation system was initially charged with 251.08 g of Dynasylan® TRIAMO (4,7,10-triazadecyltrimethoxysilane, 1.0 mol) and 80.00 g of methanol. 14.42 g of demineralized water (0.8 mol) were added dropwise within 2 minutes while stirring. In the course of this, the bottom temperature rose from 36.8° C. to 41.5° C. The mixture was stirred at a bottom temperature of 63-65° C. for a further 1 hour. Subsequently, the bottoms were cooled to 26.5° C., and 215.84 g of methacrylic anhydride (1.0 mol) were metered in within 1.5 hours. In the course of this, the bottom temperature rose to max. 56.0° C. 0.42 g of 4-hydroxy-tempo was added to the bottoms as an additional stabilizer (prior to the addition of methacrylic anhydride). A bottoms sample (35.0 g) was taken for analytical studies. 300.34 g of demineralized water were metered into the bottoms within 3 minutes. 430.5 g of distillate (methanol/water mixture) were removed at an absolute pressure of about 180 mbar and a bottom temperature of about 42° C. During the distillation, a total of 451.18 g of demineralized water were stirred into the bottoms. At the end of the distillation, the bottom temperature was 52° C. at an absolute pressure of 100 mbar. A clear, pale yellowish liquid was obtained as the bottom product.

Yield: 818.7 g

As can be seen from Table 12, the product has a solids content of 39.1%. It dissolves spontaneously in water (see Table 13).

TABLE 12

Analysis results for Example 3

| Determination | Method | Result |
|---|---|---|
| Total N [%] | see above | 4.2 |
| Solids content [%] | 3 g/8 hours/125° C. | 39.1 |
| SiO2 content [%] | AN-SAA 1171 | 6.7 |
| pH | DIN ISO 4925 | 6.1 |
| Density [g/cm³] | DIN 51757 | 1.106 |
| Viscosity [mPa · s] | DIN 53015 | 180 |
| Free methanol [%] | Based on SAA0272 | 0.2 |
| 1H and 13C NMR | Conversion level of the amidation: about 80 mol %; target product present as oligomer | |

EXAMPLE 4

A 1 l stirred apparatus with distillation system was initially charged with 332.07 g of 3-aminopropyltriethoxysilane (1.50 mol) and 81.04 g of ethanol. 21.6 g of demineralized water (1.2 mol) were added dropwise within 3 minutes while stirring. In the course of this, the bottom temperature rose from 32.3° C. to 33.5° C. The mixture was stirred at a bottom temperature of about 60° C. for a further 1 hour. Subsequently, the bottoms were cooled to 28.9° C., and 77.1 g of methacrylic anhydride (0.5 mol) were metered in within 36 minutes. In the course of this, the bottom temperature rose to max. 54° C. 0.42 g of 4-hydroxy-tempo was added to the bottoms as an additional stabilizer (prior to the addition of methacrylic anhydride). 300.11 g of demineralized water were metered into the bottoms within 3 minutes. For analytical studies, a bottoms sample (56.3 g) was taken. By adding 27.30 g of glacial acetic acid, a pH of about 7.9 was obtained. 390.9 g of distillate (ethanol/water mixture) were removed at an absolute pressure of about 146 mbar and a bottom temperature of about 40° C. During the distillation, a total of 50 g of demineralized water and 121.6 g of glacial acetic acid were stirred into the bottoms. At the end of the distillation, the bottom temperature was 50° C. at an absolute pressure of 170 mbar. The bottom product obtained was a slightly turbid, yellowish liquid, which was filtered through a pressure filter.

Yield: 531.6 g of yellowish, slightly turbid liquid.

The product dissolves spontaneously in water.

TABLE 14

Analysis result for Example 4

| Determination | Method | Result |
|---|---|---|
| Total N [%] | see above | 3.4 |
| Solids content [%] | 3 g/19 hours/125° C. | 42.4 |
| SiO2 content [%] | AN-SAA 1171 | 14.7 |
| pH | DIN ISO 4925 | 4.4 |
| Density [g/cm³] | DIN 51757 | 1.145 |
| Viscosity [mPa · s] | DIN 53015 | 76 |
| Ethanol after hydrolysis [%] | Based on SAA0272 | 1.6 |
| 1H and 13C NMR | Conversion level of the amidation: >90 mol %, target product present as oligomer | |

The invention claimed is:

1. A composition, comprising at least one water-soluble acrylamido-functional siloxanol oligomer of formula (V):

$$(R^1O)[(R^1O)_{1-a}(R^2)_a Si(C)_{1+b}O]_u[(Y)Si(C)_{1+b}O]_{u'}R^1 \cdot (HX)z \quad (V),$$

obtained by:
a) reacting a component A with an acrylic anhydride (B); and optionally
b) removing at least a portion of hydrolyzed alcohol, with optional addition of water for removal of the hydrolyzed alcohol, wherein:
the component A is at least one aminoalkyl-functionalized silicon compound selected from the group consisting of
(i) an aminoalkyl-functional alkoxysilane or a mixture of aminoalkyl-functional alkoxysilanes, each in the presence of water,
(ii) a hydrolysis or condensation product of at least one aminoalkyl-functional alkoxysilane, and
(iii) a mixture comprising at least one aminoalkyl-functional alkoxysilane and a hydrolysis product, a condensation product, or both, of the at least one aminoalkyl-functional alkoxysilane:,
C represents an acrylamido group;
Y represents $OR^1$ or, in crosslinked and/or three-dimensionally crosslinked structures, independently to $OR^1$ or $O_{1/2}$;
$R^1$ represents hydrogen;
$R^2$ represents a linear, branched or cyclic alkyl group having 1 to 8 carbon atoms;
HX is an acid, where X is an inorganic or organic acid radical;
a is 0 or 1;
b is 0 or 1;
u is an integer greater than or equal to 2;
u' is greater than or equal to 1;
z is greater than or equal to 0;
(u +u') is greater than or equal to 2; and
the composition is essentially free of diluents and releases essentially no alcohol during a crosslinking.

2. The composition according to claim 1, wherein:
the aminoalkyl-functional alkoxysilane is defined by formula (I):

$$(R^1O)_{3-a-b}(R^2)_a Si(B)_{1+b} \quad (I);$$

B independently represents a group of formula (II):

$$-(CH_2)_c-[(NH)(CH_2)_d]_e[(NH)(CH_2)_f]_g NH_{(2-h)} R^3_h \quad (II),$$

$R^1$ are each independently a linear, branched or cyclic alkyl group having 1 to 8 carbon atoms,
$R^2$ are each independently a linear, branched or cyclic alkyl group having 1 to 8 carbon atoms,
$R^3$ are each independently a linear, branched or cyclic alkyl, aryl or alkylaryl group having 1 to 8 carbon atoms,
a is 0 or 1,
b is 0, 1 or 2,
c is 1, 2, 3, 4, 5 or 6,
d is 1, 2, 3, 4, 5 or 6,
e is 0, 1, 2, 3, 4, 5 or 6,
f is 1, 2, 3, 4, 5 or 6,
g is 0, 1, 2, 3, 4, 5 and 6, and
h is independently 0 or 1,
or
B is of formula (III):

$$-(CH_2)_f-NH_{2-p}(CH_2-CH_2-NH_2)_p \quad (III),$$

j is 1, 2 or 3, and
p is 0, 1 or 2.

3. The composition according to claim 1, wherein:
the acrylic anhydride is of formula (IV):

$$(CHR^5=CR^4CO)_2O \quad (IV);$$

$R^4$ are each independently a hydrogen atom or a methyl group; and
$R^5$ are each independently a hydrogen atom or a methyl group.

4. An article, comprising the composition according to claim 1, wherein the article is selected from the group consisting of an adhesion promoter, a dental impression compound, a polymer additive, an adhesive, a sealant, and a fiber composite material.

5. The composition according to claim 1, wherein C is selected from the group consisting of $$-(CH_2)_c-[(NH)(CH_2)_d]_e[(NH)(CH_2)_f]_g NH_{(1-h)} R^3_h-(CO)CR^4=CHR^5,$$

$$-(CH_2)_f-NH(CH_2-CH_2-NH)-(CO)CR^4=CHR^5, \text{ and}$$

$$-(CH_2)_f-NH_{2-p}(CH_2-CH_2-NH-(CO)CR^4=CHR^5)_p,$$

wherein:
c 1, 2, 3, 4, 5 or 6;
d 1, 2, 3, 4, 5 or 6;
e 0, 1, 2, 3, 4, 5 or 6;
f 1, 2, 3, 4, 5 or 6;
g 0, 1, 2, 3, 4, 5 or 6;
h 0 or 1;
j 1, 2 or 3;
p 0, 1 or 2;
$R^3$ is a linear, branched or cyclic alkyl, aryl or alkylaryl group having 1 to 8 carbon atoms; and
$R^5$ a hydrogen atom or a methyl group.

* * * * *